US010190888B2

(12) United States Patent
Hryb et al.

(10) Patent No.: US 10,190,888 B2
(45) Date of Patent: Jan. 29, 2019

(54) SURGICAL STAPLING INSTRUMENTS WITH LINEAR POSITION ASSEMBLY

(71) Applicant: Covidien LP, Mansfield, MA (US)

(72) Inventors: John Hryb, Cheshire, CT (US); Ethan Collins, Naugatuck, CT (US); Luis Dussan, East Haven, CT (US); Joseph Decker, Southington, CT (US); Anthony Calderoni, Bristol, CT (US)

(73) Assignee: Covidien LP, Mansfield, MA (US)

( * ) Notice: Subject to any disclaimer, the term of this patent is extended or adjusted under 35 U.S.C. 154(b) by 377 days.

(21) Appl. No.: 15/053,599

(22) Filed: Feb. 25, 2016

(65) Prior Publication Data
US 2016/0265938 A1    Sep. 15, 2016

Related U.S. Application Data

(60) Provisional application No. 62/131,278, filed on Mar. 11, 2015.

(51) Int. Cl.
*A61B 17/072* (2006.01)
*G01D 5/14* (2006.01)
(Continued)

(52) U.S. Cl.
CPC ........... *G01D 5/145* (2013.01); *A61B 17/072* (2013.01); *A61B 17/07207* (2013.01);
(Continued)

(58) Field of Classification Search
CPC . A61B 17/068; A61B 17/072; A61B 17/1155; A61B 17/115; A61B 17/07207;
(Continued)

(56) References Cited

U.S. PATENT DOCUMENTS

| 2,777,340 A | 1/1957 | Hettwer et al. |
| 2,957,353 A | 10/1960 | Babacz |

(Continued)

FOREIGN PATENT DOCUMENTS

| CA | 2451558 A1 | 1/2003 |
| CN | 102247182 A | 11/2011 |

(Continued)

OTHER PUBLICATIONS

Extended European Search Report corresponding to counterpart International Application No. EP 14 18 4882.0 dated May 12, 2015.

(Continued)

*Primary Examiner* — Scott A. Smith

(57) ABSTRACT

A surgical stapling instrument includes an elongate body, a cartridge assembly, an anvil assembly, and a linear position assembly including a pair of opposing magnets, and a plurality of sensors. The elongate body has a central shaft longitudinally translatable therethrough. The cartridge assembly is coupled to a distal end of the elongate body. The anvil assembly is selectively connectable to the central shaft of the elongate body. The magnets are mounted to the central shaft. The sensors are fixed within the cartridge assembly and configured to sense a change in a magnetic field of the magnets upon a longitudinal movement of the magnets in response to an actuation of the central shaft to determine a linear position of the anvil assembly relative to the staple cartridge.

16 Claims, 5 Drawing Sheets

(51) Int. Cl.
   *A61B 17/00* (2006.01)
   *A61B 17/115* (2006.01)
   *A61B 17/068* (2006.01)
   *A61B 90/00* (2016.01)
   *A61B 90/98* (2016.01)

(52) U.S. Cl.
   CPC ......... *A61B 17/1155* (2013.01); *A61B 17/068* (2013.01); *A61B 17/115* (2013.01); *A61B 90/98* (2016.02); *A61B 2017/00017* (2013.01); *A61B 2017/00039* (2013.01); *A61B 2017/00119* (2013.01); *A61B 2017/00398* (2013.01); *A61B 2017/00876* (2013.01); *A61B 2017/07214* (2013.01); *A61B 2090/0811* (2016.02)

(58) Field of Classification Search
   CPC ........... A61B 2017/07214; A61B 2017/00017; A61B 2017/00234; A61B 2017/00398
   USPC .. 227/19, 175.1, 175.2, 175.3, 176.1, 180.1; 606/139, 151, 219, 153
   See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |

(56) References Cited

U.S. PATENT DOCUMENTS

| | | |
|---|---|---|
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,733,614 B2 * | 5/2014 | Ross .................. A61B 17/068 227/179.1 |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |

(56) References Cited

U.S. PATENT DOCUMENTS

| | | |
|---|---|---|
| 9,113,875 B2 | 8/2015 | Viola et al. |
| 9,113,876 B2 | 8/2015 | Zemlok et al. |
| 9,113,899 B2 | 8/2015 | Garrison et al. |
| 9,241,712 B2 | 1/2016 | Zemlok et al. |
| 9,282,961 B2 | 3/2016 | Whitman et al. |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0073981 A1* | 4/2003 | Whitman ............ A61B 10/0233 606/1 |
| 2003/0165794 A1 | 9/2003 | Matoba |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0273135 A1* | 12/2006 | Beetel ................... A61B 17/068 227/175.1 |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0283571 A1* | 11/2008 | Boyden ................ A61B 17/068 227/175.1 |
| 2008/0308603 A1 | 12/2008 | Shelton et al. |
| 2009/0012533 A1 | 1/2009 | Barbagli et al. |
| 2009/0057369 A1* | 3/2009 | Smith ............... A61B 17/07207 227/175.1 |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0206132 A1* | 8/2009 | Hueil ............... A61B 17/07207 227/175.2 |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0065609 A1* | 3/2010 | Schwemberger .... A61B 17/115 227/180.1 |
| 2010/0069942 A1 | 3/2010 | Shelton, IV |
| 2010/0096435 A1* | 4/2010 | Fuchs ................. A61B 17/1114 227/179.1 |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0062211 A1* | 3/2011 | Ross ................ A61B 17/07207 227/175.1 |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0144640 A1* | 6/2011 | Heinrich ............ A61B 17/0469 606/41 |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0253329 A1 | 10/2012 | Zemlok et al. |
| 2012/0292367 A1* | 11/2012 | Morgan ................ A61B 17/072 227/175.1 |
| 2012/0310220 A1 | 12/2012 | Malkowski et al. |
| 2012/0323226 A1 | 12/2012 | Chowaniec et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0206814 A1* | 8/2013 | Morgan ........... A61B 17/07207 227/176.1 |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0001231 A1* | 1/2014 | Shelton, IV ..... A61B 17/07207 227/175.3 |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0110456 A1* | 4/2014 | Taylor ................. A61B 17/072 227/176.1 |
| 2014/0166717 A1* | 6/2014 | Swayze ............. A61B 17/1155 227/4 |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0263538 A1* | 9/2014 | Leimbach ........ A61B 17/07207 227/175.1 |
| 2014/0276932 A1 | 9/2014 | Williams et al. |
| 2014/0299647 A1 | 10/2014 | Scirica et al. |

(56) References Cited

U.S. PATENT DOCUMENTS

| | | |
|---|---|---|
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0083774 A1* | 3/2015 | Measamer .......... A61B 17/068 227/175.1 |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0342601 A1 | 12/2015 | Williams et al. |

FOREIGN PATENT DOCUMENTS

| | | | |
|---|---|---|---|
| DE | 102008053842 A1 | 5/2010 | |
| EP | 0705571 A1 | 4/1996 | |
| EP | 1769754 A1 | 4/2007 | |
| EP | 2316345 A1 | 5/2011 | |
| EP | 2668910 A2 | 12/2013 | |
| ES | 2333509 A1 | 2/2010 | |
| JP | 2005-125075 A | 5/2005 | |
| KR | 20120022521 A | 3/2012 | |
| WO | 2011/108840 A2 | 9/2011 | |
| WO | 2012/040984 A1 | 4/2012 | |

OTHER PUBLICATIONS

Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.

* cited by examiner

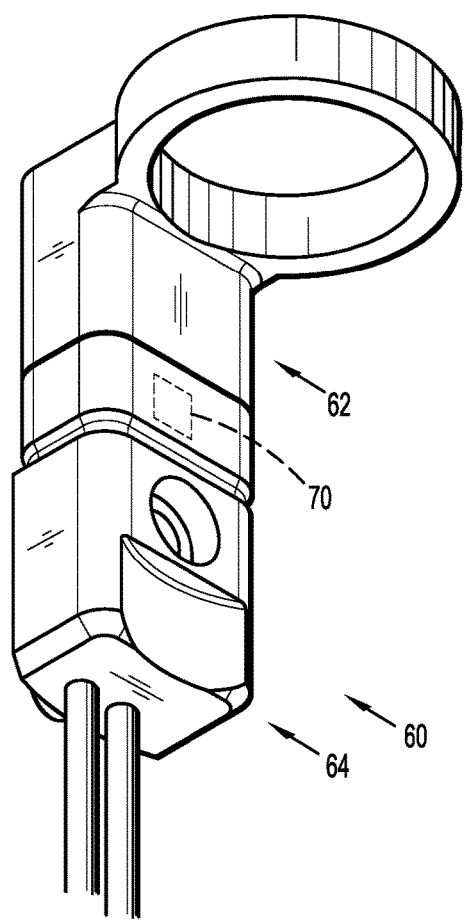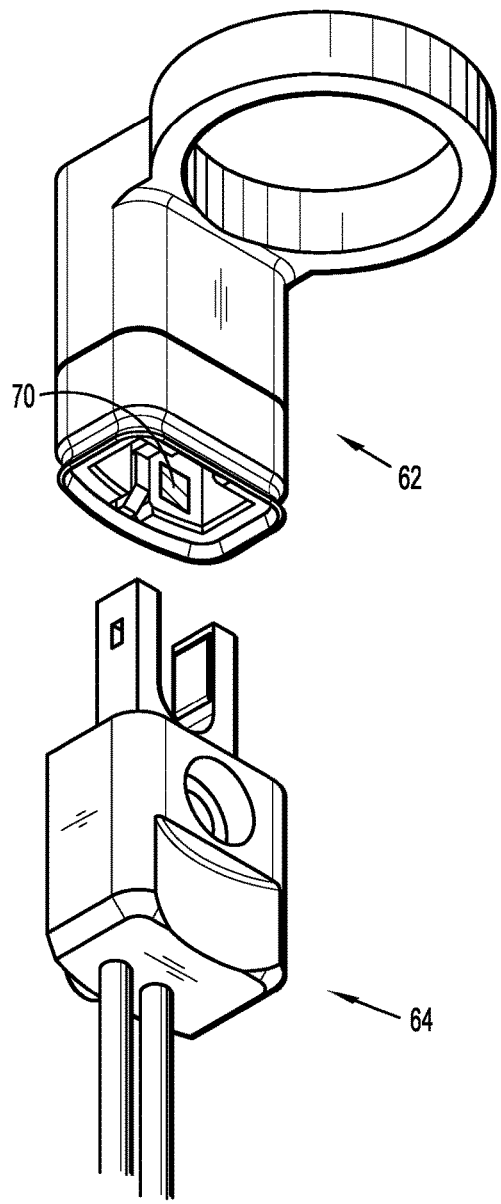
FIG. 5A
FIG. 5B

SURGICAL STAPLING INSTRUMENTS WITH LINEAR POSITION ASSEMBLY

CROSS-REFERENCE TO RELATED APPLICATIONS

This application claims the benefit of and priority to U.S. Provisional Patent Application Ser. No. 62/131,278 filed Mar. 11, 2015, the entire disclosure of which is incorporated by reference herein.

BACKGROUND

1. Technical Field

The present disclosure is directed to surgical instruments, such as surgical stapling instruments. In particular, the present disclosure relates to surgical instruments and loading units having assemblies for determining relative linear positions of components of the surgical instrument.

2. Background of Related Art

Surgical stapling instruments having an end effector configured to clamp and suture tissue are well known in the medical arts. Typically, these instruments include a first jaw that supports an anvil assembly and a second jaw that supports a cartridge assembly which houses a plurality of staples. The first and second jaws are movable in relation to each other between spaced and approximated positions to clamp tissue between the jaws prior to firing the staples into the tissue. The first and second jaws may also support two part fasteners or first and second compression members that interact to suture tissue.

Circular stapling instruments are used to perform end-to-end anastomosis procedures within a patient. During an end-to-end anastomosis procedure, an end of a first vessel portion is joined to an end of a second vessel portion. Typically, circular stapling instruments include an anvil, which defines an annular array of staple deforming depressions and an annular cartridge housing annular rows of staples. During actuation of the circular stapling instrument, the anvil is approximated toward the annular cartridge to clamp tissue therebetween. When it is determined that the tissue has been clamped between the anvil and the annular cartridge, staples may then be ejected into the clamped tissue.

Accordingly, it would be beneficial to have a system for precisely determining and indicating the relative positions of an anvil and a cartridge throughout actuation of a surgical stapling instrument.

SUMMARY

In one aspect of the present disclosure, a surgical stapling instrument is provided. The surgical stapling instrument includes an elongate body, a cartridge assembly, an anvil assembly, and a linear position assembly having a pair of opposing magnets, and a plurality of sensors. The elongate body has a proximal end and a distal end and includes a longitudinally translatable central shaft. The cartridge assembly is coupled to the distal end of the elongate body and defines a longitudinal axis. The cartridge assembly includes a staple cartridge. The anvil assembly is selectively connectable to a distal end of the central shaft of the elongate body. The opposing magnets of the linear position assembly are mounted to the central shaft. Each magnet generates a magnetic field. The sensors are fixed within the cartridge assembly and are configured to sense a change in the magnetic field upon a longitudinal movement of the pair of opposing magnets in response to an actuation of the central shaft to determine a linear position of the anvil assembly along the longitudinal axis relative to the staple cartridge.

In some embodiments, the sensors may be three magnetoresistance sensors or three hall-effect sensors. The sensors may be axially aligned with one another along the longitudinal axis of the cartridge assembly.

It is contemplated that the opposing magnets may be in the form of two magnetic bars each having a north pole and a south pole. The two magnetic bars may be oriented such that the north poles of the two magnetic bars are adjacent one another or the south poles of the two magnetic bars are adjacent one another.

It is envisioned that the sensors may be laterally offset and parallel with the pair of opposing magnets.

In some aspects, the linear position assembly may further include a micro-controller in electrical communication with the sensors. The micro-controller may be configured to determine the linear position of the anvil assembly along the longitudinal axis relative to the staple cartridge. The micro-controller may determine the linear position of the anvil assembly by: determining a linear position of the plurality of magnets relative to each sensor of the plurality of sensors; determining which sensor of the plurality of sensors has a highest peak-to-peak voltage value; and determining which sensor of the plurality of sensors has a second highest peak-to-peak voltage value.

In some embodiments, the surgical stapling instrument may further include a chip assembly at least partially disposed within the cartridge assembly. The chip assembly may have the sensors fixed thereto.

In another aspect of the present disclosure, a method of determining a linear position of a component of the surgical stapling instrument is provided. The method includes providing the surgical stapling instrument; sensing, via a plurality of sensors of a linear position assembly, longitudinal movement of a pair of opposing magnets of the linear position assembly upon actuation of the central shaft; and determining a linear position of the anvil assembly relative to the staple cartridge along the longitudinal axis.

In some embodiments, the method may further include at least one of: determining an angle of direction of the magnetic field emitted by the pair of opposing magnets; or determining a magnetic flux density of the magnetic field emitted by the pair of opposing magnets.

It is contemplated that determining the linear position of the anvil assembly may include: determining a linear position of the plurality of magnets relative to each sensor of the plurality of sensors; determining which sensor of the plurality of sensors has a highest peak-to-peak voltage value; and determining which sensor of the plurality of sensors has a second highest peak-to-peak voltage value.

It is envisioned that determining the linear position of the anvil assembly may include determining a linear position of an anvil head of the anvil assembly relative to a distal end of the staple cartridge.

BRIEF DESCRIPTION OF THE DRAWINGS

Embodiments of the presently disclosed surgical stapling instruments are disclosed herein, with reference to the following drawings:

FIG. 5A is a perspective view of the chip assembly of FIG. 4; and

FIG. 5B is a perspective view, with parts separated, of the chip assembly of FIG. 4.

DETAILED DESCRIPTION

Figure 1:
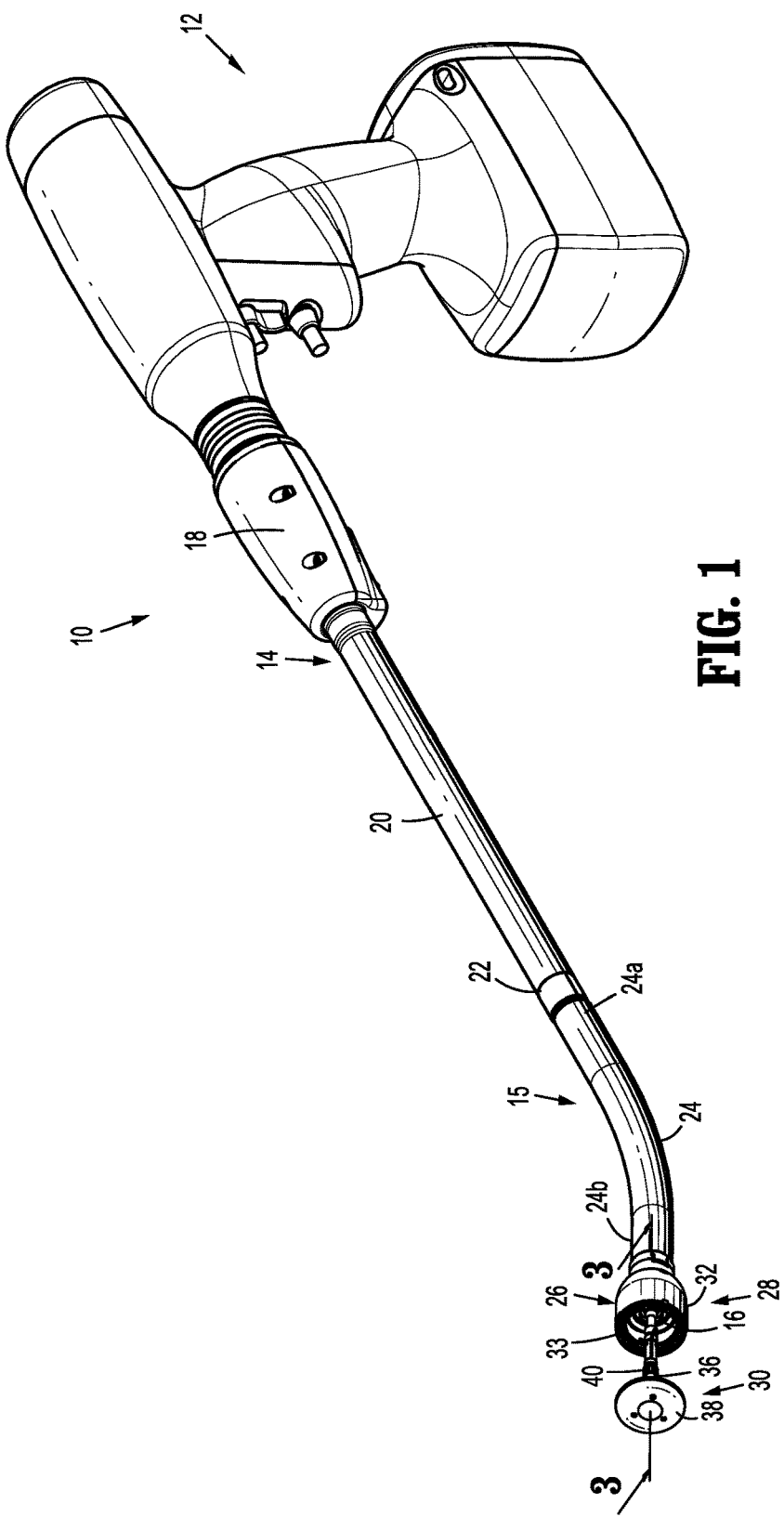
FIG. 1 is a perspective view of a surgical stapling instrument in accordance with embodiments of the present disclosure.

Persons having skill in the art will understand the present disclosure from reading the following description in conjunction with the accompanying drawings. Reference characters indicate the same or similar elements throughout the drawings. As is customary, the term "distal" refers to a location farther from the user of the instrument and the term "proximal" refers to a location that is closer to the user of the instrument.

FIG. 1 illustrates an embodiment of a surgical stapling instrument according to the present disclosure, referenced generally as a circular stapler 10. Circular stapler 10 includes a handle assembly 12, an adapter assembly 14, which is supported by and extends distally from handle assembly 12, and a surgical loading unit 15 coupled to a distal end 22 of adapter assembly 14. Adapter assembly 14 is reusable and includes a knob housing 18 that is releasably coupled to a distal end of handle assembly 12, and an elongated body portion 20 that extends distally from knob housing 18. Elongated body portion 20 has a distal end 22 that is configured to be coupled to an elongate body 24 of loading unit 15. Adapter assembly 14 converts a rotation of drive elements (not shown) of handle assembly 12 into axial movement of driven members (not shown) of adapter assembly 14 to actuate functions of loading unit 15. A similar adapter assembly is disclosed in U.S. Patent Application Publication No. 2013/0324978, which is incorporated herein in its entirety by reference.

In some embodiments, circular stapler 10 may have an elongated body portion that is integrally formed with a manually actuatable handle assembly instead of an adapter assembly. One example of such a stapler is disclosed in U.S. Pat. No. 7,802,712, which is incorporated herein in its entirety by reference.

Loading unit 15 includes an elongate body 24 and an end effector 26 supported on elongate body 24. Elongate body 24 has a proximal end 24a releasably coupled to distal end 22 of elongated body portion 20 of adapter assembly 14. In some embodiments, elongate body 24 may be monolithically formed with or integrally connected to distal end 22 of elongated body portion 20.

Figure 3:
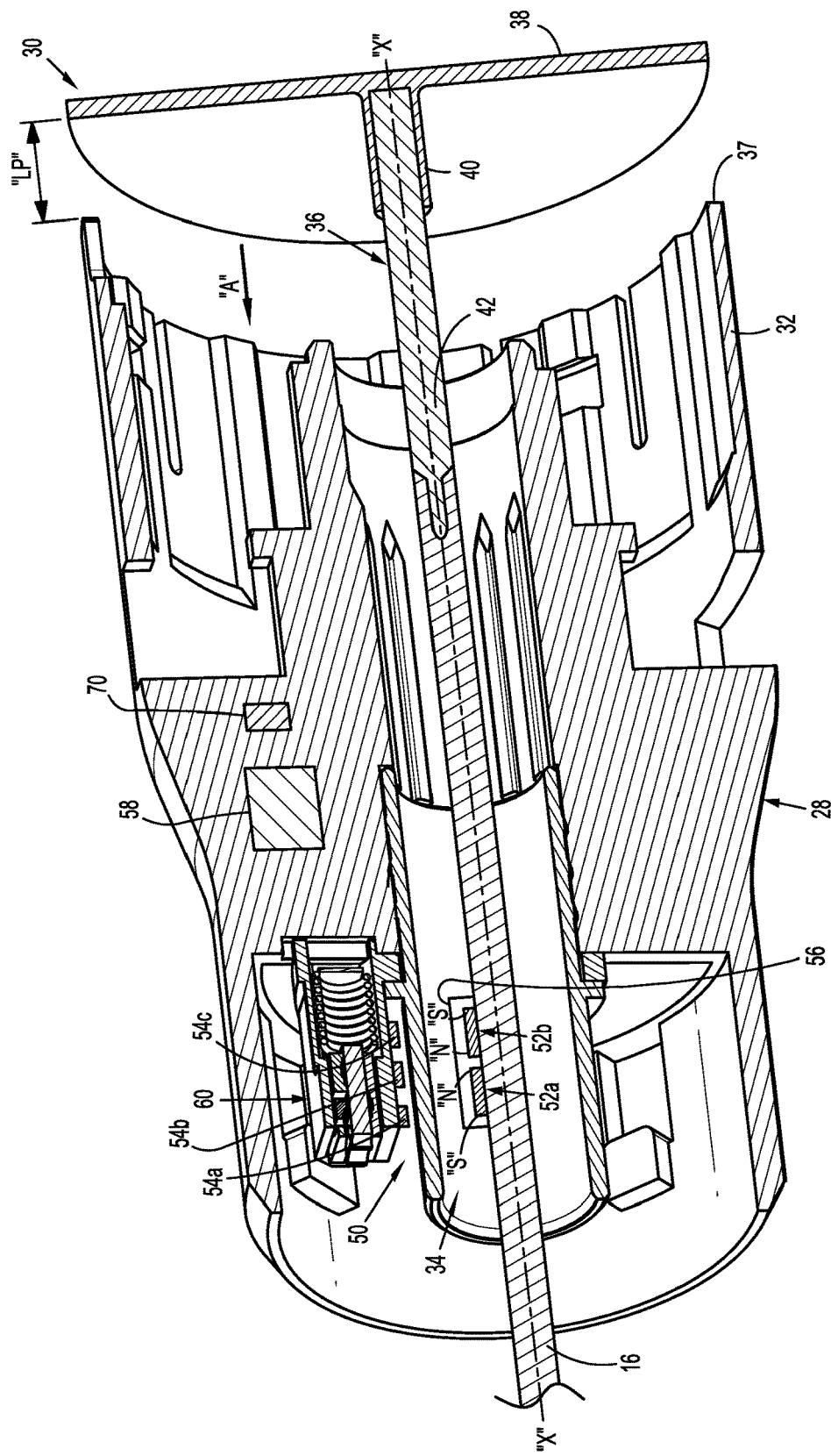
FIG. 3 is a cross-sectional view, taken along section line 3-3 in FIG. 1, of components of an end effector of the surgical stapling instrument including a linear position assembly.

With reference to FIGS. 1 and 3, end effector 26 of loading unit 15 includes a cartridge assembly 28 and an anvil assembly 30. Cartridge assembly 28 is releasably mounted to a distal end 24b of elongate body 24 and defines a longitudinal axis "X." Cartridge assembly 28 includes a staple cartridge 32 configured for supporting a plurality of surgical staples (not shown) therein and to discharge the staples into tissue after approximation of cartridge assembly 28 and anvil assembly 30. Staple cartridge 32 defines a longitudinal channel 34 for movable receipt of an anvil shaft 36 of anvil assembly 30. Staple cartridge 32 has a plurality of staple retaining recesses 33 having the surgical staples disposed therein. Staple retaining recesses 33 are arranged in annular rows. It is envisioned that cartridge assembly 28 may be operably mounted to a distal end of any actuation assembly, powered or manual, of various surgical instruments.

Anvil assembly 30 includes, inter alia, an anvil shaft 36, an anvil head 38, and an anvil center rod 40 extending from anvil head 38. Anvil shaft 36 extends from elongate body 24 of loading unit 15 and is movably disposed within channel 34 of cartridge assembly 28 along longitudinal axis "X." A proximal end (not shown) of anvil shaft 36 is configured to be removably or non-removably coupled to a central shaft 16 of adapter assembly 14. As known in the art, central shaft 16 of adapter assembly 14 is operable to selectively longitudinally move anvil shaft 36 to move anvil head 38, which is supported on anvil shaft 36, between unapproximated and approximated positions, in relation to cartridge assembly 28, in response to actuation of handle assembly 12.

A proximal end 42 of anvil shaft 36 extends proximally from anvil head 38 and is configured for selective connection with a distal end of central shaft 16 of adapter assembly 14, to secure anvil assembly 30 to adapter assembly 14. As such, longitudinal movement of anvil shaft 36, via an actuation of handle assembly 12, results in a corresponding longitudinal movement of anvil head 38 relative to cartridge assembly 28 to clamp tissue between cartridge and anvil assemblies 28, 30. In some embodiments, anvil shaft 36 may be monolithically formed with central shaft 16. Reference may be made to U.S. Pat. No. 7,802,712 for a detailed description of the construction and operation of an end effector including a cartridge assembly and an anvil assembly similar to that disclosed herein.

With reference to FIG. 3, circular stapler 10 includes a linear position assembly 50 including a pair of magnets 52a, 52b and a plurality of sensors 54a, 54b, 54c. Magnets 52a, 52b are in the form of magnetic bars. In some embodiments, magnets 52a, 52b may be variously shaped, such as, for example, cylindrical, rounded, squared, oval, polygonal, uniform, or non-uniform. Magnets 52a, 52b generate a magnetic field that is detected by sensors 54a, 54b, 54c and used to ultimately determine a linear position "LP" of anvil assembly 30 relative to cartridge assembly 28, as will be described in detail below.

Magnets 52a, 52b are mounted to central shaft 16 of adapter assembly 14. In particular, magnets 52a, 52b are attached to an outer surface of central shaft 16 such that magnets 52a, 52b move with central shaft 16, along longitudinal axis "X," as central shaft 16 moves relative to cartridge assembly 28 between the unapproximated and approximated positions. In some embodiments, magnets 52a, 52b may be supported on or disposed in various components of anvil assembly 30, for example, various regions of anvil shaft 36, anvil head 38 and/or anvil rod 40.

Figure 2:
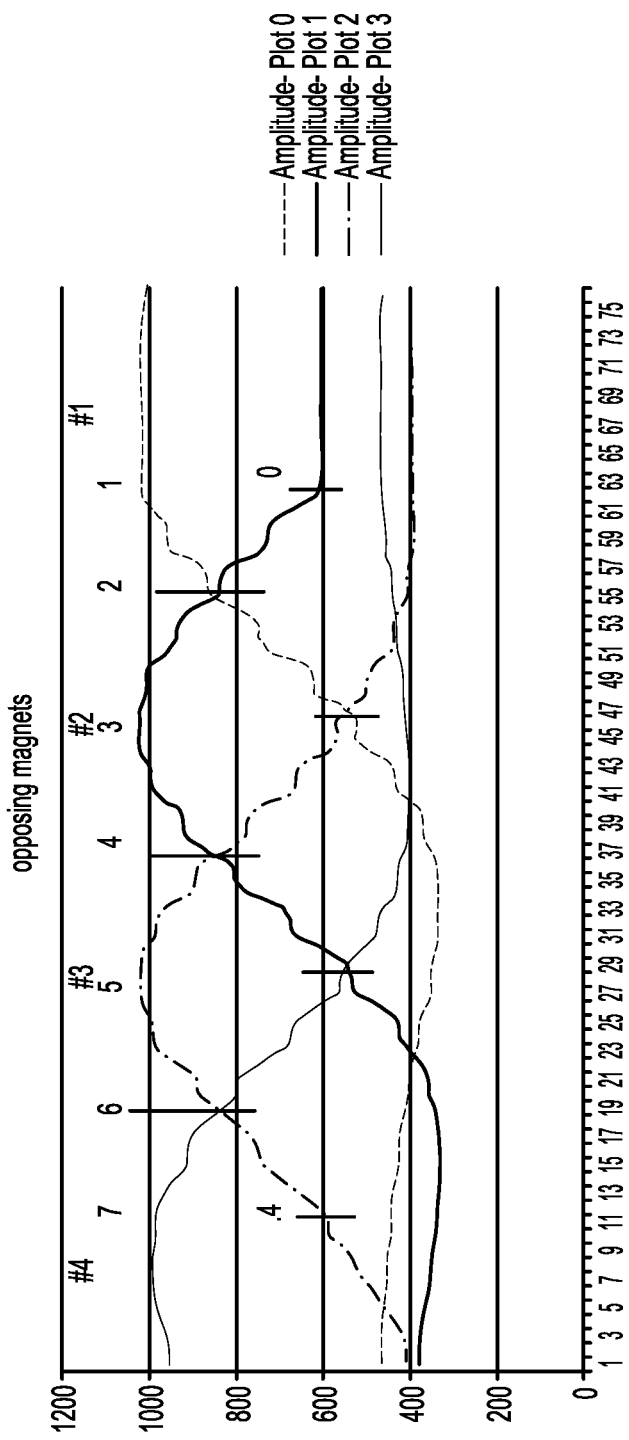
FIG. 2 is a graphic illustration of points of interest along response curves for linear distance measurements using a pair of magnets and four magnetic sensors.

Magnets 52a, 52b each have a north pole "N" and a south pole "S." Magnets 52a, 52b are oriented in a side-by-side orientation relative to one another such that magnets 52a, 52b have their respective opposing poles (i.e., north-north or south-south) adjacent one another. In this way, the magnetic field generated by each magnet 52a, 52b causes magnets 52a, 52b to repel one another. As illustrated in FIG. 2, magnets 52a, 52b, positioned with their magnetic fields opposing one another, results in a unique magnetic field being generated that is easier to formulate a linear distance therefrom as compared to using distinctive magnetic waveforms. In some embodiments, magnets 52a, 52b are positioned relative to one another with their attracting poles (i.e., north-south) adjacent one another, and four (4) sensors may be fixedly positioned within cartridge assembly 28 which function together to produce the plots shown in FIG. 2 as magnets 52a, 52b translate axially across a linear array of the four magnetic sensors.

A housing or casing 56 attached to central shaft 16 encloses magnets 52a, 52b to maintain magnets 52a, 52b positioned adjacent one another in their opposing configuration. Alternately, magnets 52a, 52b may be affixed to central shaft 16 or may be embedded into central shaft 16.

With continued reference to FIG. 3, circular stapler 10, and more specifically cartridge assembly 28, includes three sensors 54a, 54b, 54c that act in conjunction with magnets 52a, 52b and a microcontroller 58 to determine the gap or linear position "LP" between distal end 37 of staple cartridge 32 and anvil head 38 of anvil assembly 30. In some embodiments, more or less than three sensors may be provided. Sensors 54a-c are fixedly attached to a chip assembly 60, as will be described in greater detail below. In some embodiments, sensors 54a-c may be fixed to various portions of cartridge assembly 30. Sensors 54a-c are axially aligned with one another along longitudinal axis "X" such that sensors 54a-c are laterally offset and parallel with magnets 52a, 52b.

Sensors 54a-c are configured to sense a change in the magnetic field emitted by magnets 52a, 52b upon longitudinal movement of magnets 52a, 52b relative to sensors 54a-c as central shaft 16 is displaced or moved axially. Sensors 54a-c are in the form of magnetoresistance sensors. As such, magnetoresistance sensors 54a-c are configured to sense or determine an angle of direction of the magnetic field emitted by magnets 52a, 52b throughout relative longitudinal movement of magnets 52a, 52b. In some embodiments, sensors 54a-c may be in the form of hall-effect sensors. Hall-effect sensors are configured to sense or determine a magnetic flux density of the magnetic field emitted by magnets 52a, 52b throughout relative longitudinal movement of magnets 52a, 52b.

Circular stapler 10 may include a display unit and/or indicator (not shown) for displaying information, for example, the relative linear position of anvil shaft 36 and cartridge assembly 28. Additionally or alternatively, circular stapler 10 may include an audio component for sounding an audible alarm or recorded message. The display can be a light emitting diode, liquid crystal display, or any other display.

Circular stapler 10 includes a controller, such as, for example, a microcontroller 58. Microcontroller 58 is in electrical communication with each of sensors 54a-c. Microcontroller 58 is connected to sensors 54a-c by wires, leads, or via wireless connection. Sensors 54a-c relay, to microcontroller 58, the sensed angle of direction of the magnetic field of magnets 52a, 52b or the sensed magnetic flux density of the magnetic field of magnets 52a, 52b. Microcontroller 58 is configured to determine, based on the information relayed by sensors 54a-c, a linear position of anvil assembly 30 along longitudinal axis "X" relative to cartridge assembly 28, as will be described in greater detail below. Microcontroller 58 includes tables of information that indicate the desired gap or linear position "LP" for a particular loading unit (based on staple size, staple line length, etc.) and can be used to prevent the firing of staples in the event that the desired gap cannot be achieved. For example, U.S. Patent Publication No. 2012/0211542 discloses tissue management modes for controlling a surgical instrument and utilizes stored correlation tables, the entire contents of which being incorporated by reference herein.

Microcontroller 58 can be an integrated circuit, analog or logic circuitry, and/or microprocessor, or an array of such components. Microcontroller 58 receives information from a memory unit 70, other sensors in adapter assembly 14 and/or loading unit 15, and can control the operation of circular stapling instrument 10. Microcontroller 58 can initiate a visual or audible alarm in the event that a selected gap between anvil assembly 30 and cartridge assembly 28 is achieved, or microcontroller 58 can cease operation of circular stapler 10 by halting a motor (not shown) of handle assembly 12.

Figure 4:
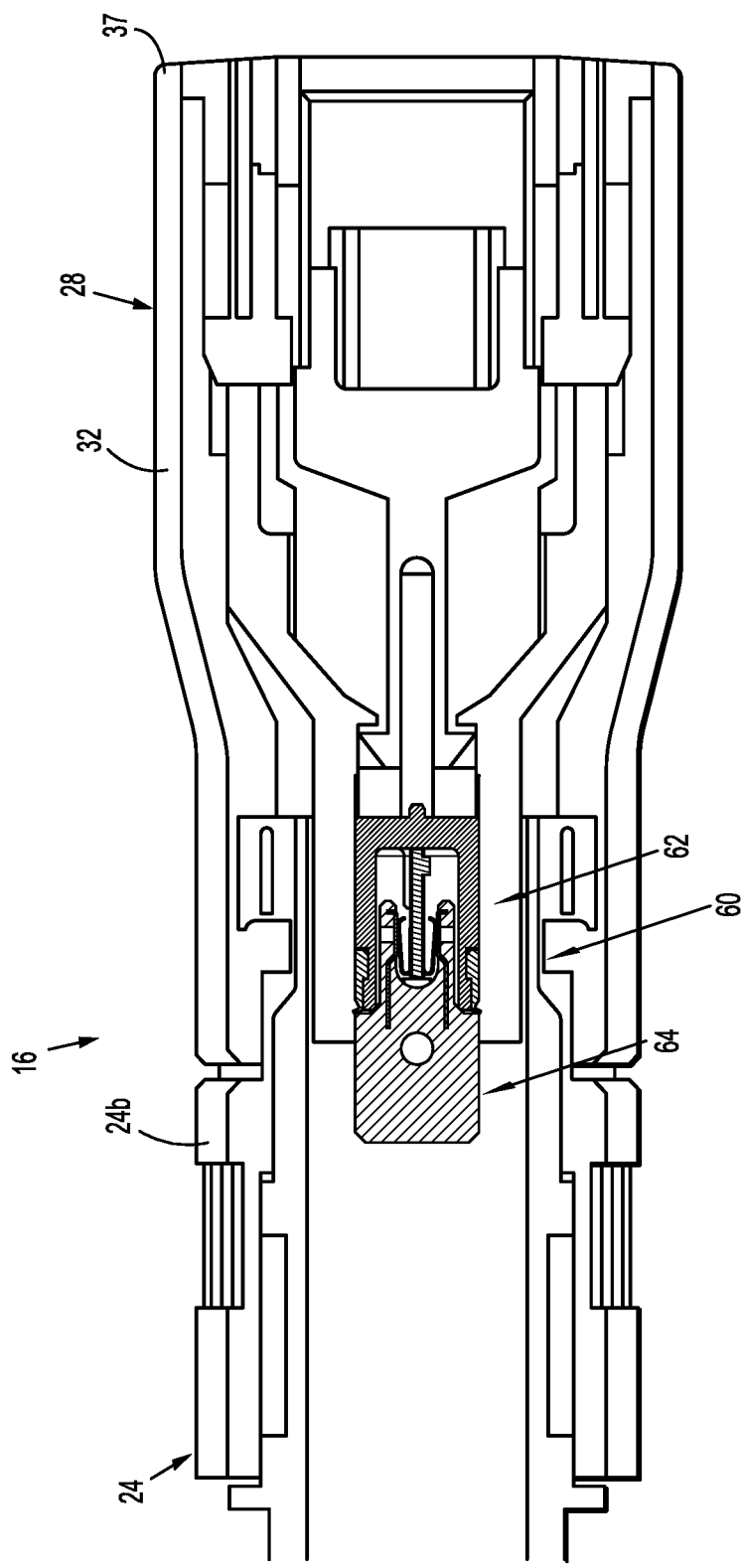
FIG. 4 is a cross-sectional view of a distal end of the surgical stapling instrument of FIG. 1 illustrating a chip assembly of the linear position assembly.

With reference to FIGS. 4, 5A and 5B, loading unit 15 further includes a chip assembly 60. Chip assembly 60 includes a housing assembly 62 and a plug assembly 64 configured to be releasably engaged to one another upon assembly of cartridge assembly 28 with distal end 24b of elongate body 24 of loading unit 15. Housing assembly 62 is configured to be securely mounted within cartridge assembly 28, and plug assembly 64 is configured to be securely mounted within distal end 24b of elongate body 24. Housing assembly 62 and plug assembly 64 are positioned within respective cartridge assembly 28 and elongate body 24 such that when cartridge assembly 28 is secured to distal end 24b of elongate body 24, housing assembly 62 engages plug assembly 64. It is envisioned that one or both of housing assembly 62 and plug assembly 64 may be spring biased towards the other to overcome any manufacturing tolerances between cartridge assembly 28 and elongate body 24.

Chip assembly 60 includes memory unit or chip 70 mentioned above. Chip 70 may be any suitable commercially available chip capable of storing the specifications of end effector 26 including, but not limited to, a distance between magnets 52a, 52b, a distance between each magnet 52a, 52b and anvil head 38, a distance between sensors 54a-c, and a distance between each sensor 54a-c and distal end 37 of staple cartridge 32, and transmitting the specifications to microprocessor 58. In one embodiment, chip 70 includes an erasable programmable read only memory ("EPROM") chip.

Upon housing assembly 62 being connected to plug assembly 64, within adapter assembly 14, it is envisioned that chip 70 will automatically transmit the specifications of end effector 26 to microprocessor 58 so that microprocessor 58 can determine the relative positions of anvil assembly 30 and cartridge assembly 28 during actuation of anvil assembly 30 using the stored information from memory unit 70 and the sensed information provided by sensors 54a-c, as will be described in detail below.

Referring to FIG. 3, in an operation of circular stapler 10, an unknown and changing linear position "LP" of anvil head 38 relative to distal end 37 of staple cartridge 32 is to be determined throughout an actuation of circular stapler 10. As circular stapler 10 is actuated, the central shaft 16 moves anvil shaft 36 proximally, in the direction indicated by arrow "A" in FIG. 3. Proximal longitudinal movement of anvil shaft 36 approximates anvil head 38 toward distal end 37 of staple cartridge 32 via the fixed engagement or connection between central shaft 16 of adapter assembly 14 and anvil shaft 36 of anvil assembly 30. Proximal longitudinal movement of central shaft 16 effects linear movement of magnets 52a, 52b relative to sensors 54a-c since magnets 52a, 52b are fixedly engaged to proximally moving central shaft 16.

The linear movement of magnets 52a, 52b relative to sensors 54a-c changes both the magnetic flux density of the magnetic field emitted by magnets 52a, 52b relative to sensors 54a-c and the angle of direction of the magnetic field emitted by magnets 52a, 52b relative to sensors 54a-c. As mentioned above, magnets 52a, 52b being positioned with their magnetic fields opposing one another results in a unique magnetic field being generated that permits formulation or calculation of a linear distance therefrom as compared to using distinctive magnetic waveforms.

In the embodiments wherein sensors 54a-c are magnetoresistance sensors, sensors 54a-c sense the change in the angle of direction of the magnetic field of magnets 52a, 52b. In the embodiments wherein sensors 54a-c are hall-effect sensors, sensors 54a-c sense the change in the magnetic flux density of the magnetic field of magnets 52a, 52b. In embodiments, sensors 54a-c may sense both the change in the angle of direction and the magnetic flux density of the magnets 52a, 52b.

Each sensor 54a-c converts the sensed magnetic field to a voltage output that corresponds to the linear position of magnets 52a, 52b relative to each sensor 54a-c. Sensors 54a-c relay the voltage output to microcontroller 58, which determines which sensor 54a, 54b, or 54c of sensors 54a-c has a highest peak-to-peak voltage value and which sensor 54a, 54b, or 54c of sensors 54a-c has a second highest peak-to-peak voltage value. Using this information, microcontroller 58 determines the linear distance (i.e., distance along longitudinal axis "X") between magnets 52a, 52b and sensors 54a-c by comparing the determined first and second highest peak-to-peak voltage values to known peak-to-peak voltage values for sensors of a similar type sensors 54a-c. The known peak-to-peak voltage values correspond to a known linear distance between two, adjacent magnets and three, adjacent sensors.

Once the linear position of magnets 52a, 52b relative to sensors 54a-c is determined, microcontroller 58 determines the linear position "LP" between anvil head 38 and distal end 37 of staple cartridge 32. Microcontroller 58 determines the linear position "LP" using the information received from sensors 54a-c pertaining to the linear position of magnets 52a, 52b relative to sensors 54a-c, and the information stored in chip 70 of chip assembly 60, which includes the distance between magnets 52a, 52b and anvil head 38, and the distance between sensors 54a-c and distal end 37 of staple cartridge 32, and the known sizes and dimensions of the components of cartridge assembly 28 and anvil assembly 30. The linear position "LP" is determined dynamically at various points in time throughout actuation of end effector 26. The determined linear positions "LP" are displayed on a screen (not shown) to be visually identified by a clinician who can use the information to gain insight about tissue thickness, when to fire staples into clamped tissue, etc.

In any of the embodiments disclosed herein, electronic sensors, optical sensors, magnetic sensors, and/or any other kind of sensors, can be used in addition to sensors 54a-c described herein to provide information about the particular loading unit and its use. In a stapling instrument of the type referenced herein, the sensors 54a-c and/or magnets 52a, 52b may be provided along any component or components which move during operation. For example, an electronic sensor, hall-effect sensor, magnetoresistance sensor, optic sensor, or other sensor, and/or magnets may be provided on any component of anvil assembly 30 or cartridge assembly 28, including chip assembly 60, anvil shaft 36, anvil head 38, channel 34, distal end 37 of staple cartridge 32, or any combination thereof.

In some embodiments, microcontroller 58 may include one or more microprocessors or chips. Microcontroller 58 may include more than one such chips or processors, and can be an array of such elements. Data for determining the type and characteristics of end effectors, adapter assemblies and/or handle portions can be stored in memory units in the form of graphs, charts, tables, arrays, or the like. This can be used in conjunction with other systems provided for circular stapler 10.

While the present disclosure has been described and illustrated in connection with certain embodiments, it is not the intention of the applicant to restrict or in any other way limit the scope of the claims to such detail. Additional advantages and modifications will be readily apparent to those skilled in the art.

What is claimed is:

1. A surgical stapling instrument, comprising:
    an elongate body having a proximal end and a distal end, the elongate body including a longitudinally translatable central shaft;
    a cartridge assembly coupled to the distal end of the elongate body and defining a longitudinal axis, the cartridge assembly including a staple cartridge;
    an anvil assembly selectively connectable to a distal end of the central shaft; and
    a linear position assembly including:
        a pair of opposing magnets mounted to the central shaft, wherein each magnet generates a magnetic field, the pair of opposing magnets each having a north pole and a south pole and being oriented such that the north poles of the pair of opposing magnets are adjacent one another or the south poles of the pair of opposing magnets are adjacent one another; and
        a plurality of sensors fixed within the cartridge assembly and configured to sense a change in the magnetic fields upon a longitudinal movement of the pair of opposing magnets in response to an actuation of the central shaft to determine a linear position of the anvil assembly along the longitudinal axis relative to the staple cartridge.

2. The surgical stapling instrument according to claim 1, wherein the plurality of sensors is at least one of:
    at least three magnetoresistance sensors; or
    at least three hall-effect sensors.

3. The surgical stapling instrument according to claim 2, wherein the plurality of sensors is axially aligned with one another along the longitudinal axis of the cartridge assembly.

4. The surgical stapling instrument according to claim 1, wherein the plurality of sensors is laterally offset and parallel with the pair of opposing magnets.

5. The surgical stapling instrument according to claim 1, wherein the linear position assembly further includes a micro-controller in electrical communication with the plurality of sensors, the micro-controller configured to determine the linear position of the anvil assembly along the longitudinal axis relative to the staple cartridge.

6. The surgical stapling instrument according to claim 5, wherein the micro-controller is configured to determine the linear position of the anvil assembly by:
    determining a linear position of the plurality of magnets relative to each sensor of the plurality of sensors;
    determining which sensor of the plurality of sensors has a highest peak-to-peak voltage value; and
    determining which sensor of the plurality of sensors has a second highest peak-to-peak voltage value.

7. The surgical stapling instrument according to claim 1, wherein the linear position assembly further includes a chip assembly at least partially disposed within the cartridge assembly and having the plurality of sensors fixed thereto.

8. A method of determining a linear position of a component of a surgical stapling instrument, comprising:
providing a surgical stapling instrument including:
an elongate body having a proximal end and a distal end, the elongate body including a longitudinally translatable central shaft;
a cartridge assembly coupled to the distal end of the elongate body and defining a longitudinal axis, the cartridge assembly including a staple cartridge;
an anvil assembly selectively connectable to a distal end of the central shaft of the elongate body; and
a linear position assembly including:
a pair of opposing magnets mounted to the central shaft, wherein each magnet generates a magnetic field; and
a plurality of sensors fixed within the cartridge assembly;
sensing, via the plurality of sensors, longitudinal movement of the pair of opposing magnets upon actuation of the central shaft; and
determining a linear position of the anvil assembly relative to the staple cartridge along the longitudinal axis, wherein determining the linear position of the anvil assembly includes:
determining a linear position of the plurality of magnets relative to each sensor of the plurality of sensors;
determining which sensor of the plurality of sensors has a highest peak-to-peak voltage value; and
determining which sensor of the plurality of sensors has a second highest peak-to-peak voltage value.

9. The method according to claim 8, further comprising at least one of:
determining an angle of direction of the magnetic field emitted by the pair of opposing magnets; or
determining a magnetic flux density of the magnetic field emitted by the pair of opposing magnets.

10. The method according to claim 8, wherein the pair of opposing magnets are in the form of two magnetic bars each having a north pole and a south pole, the two magnetic bars being oriented such that the north poles of the two magnetic bars are adjacent one another or the south poles of the two magnetic bars are adjacent one another.

11. The method according to claim 8, wherein determining the linear position of the anvil assembly includes determining a linear position of an anvil head of the anvil assembly relative to a distal end of the staple cartridge.

12. A surgical stapling instrument, comprising:
an elongate body having a proximal end and a distal end, the elongate body including a longitudinally translatable central shaft;
a cartridge assembly coupled to the distal end of the elongate body and defining a longitudinal axis, the cartridge assembly including a staple cartridge;
an anvil assembly selectively connectable to a distal end of the central shaft; and
a linear position assembly including:
a pair of opposing magnets mounted to the central shaft, wherein each magnet generates a magnetic field;
a plurality of sensors fixed within the cartridge assembly and configured to sense a change in the magnetic fields upon a longitudinal movement of the pair of opposing magnets in response to an actuation of the central shaft to determine a linear position of the anvil assembly along the longitudinal axis relative to the staple cartridge; and
a micro-controller in electrical communication with the plurality of sensors, wherein the micro-controller is configured to determine the linear position of the anvil assembly along the longitudinal axis relative to the staple cartridge by:
determining a linear position of the plurality of magnets relative to each sensor of the plurality of sensors;
determining which sensor of the plurality of sensors has a highest peak-to-peak voltage value; and
determining which sensor of the plurality of sensors has a second highest peak-to-peak voltage value.

13. The surgical stapling instrument according to claim 12, wherein the plurality of sensors is at least one of:
at least three magnetoresistance sensors; or
at least three hall-effect sensors.

14. The surgical stapling instrument according to claim 12, wherein the plurality of sensors is axially aligned with one another along the longitudinal axis of the cartridge assembly.

15. The surgical stapling instrument according to claim 12, wherein the plurality of sensors is laterally offset and parallel with the pair of opposing magnets.

16. The surgical stapling instrument according to claim 12, wherein the linear position assembly further includes a chip assembly at least partially disposed within the cartridge assembly and having the plurality of sensors fixed thereto.

* * * * *